United States Patent
Sako et al.

(10) Patent No.: US 9,901,641 B2
(45) Date of Patent: Feb. 27, 2018

(54) SILYL ETHERIFIED DERIVATIVES OF 5-AZACYTIDINES IN CARBOHYDRATE MOIETY

(71) Applicant: OHARA PHARMACEUTICAL CO., LTD., Koka-cho, Koka-shi, Shiga (JP)

(72) Inventors: Magoichi Sako, Shiga (JP); Shinpei Sugiyama, Shiga (JP)

(73) Assignee: Ohara Pharmaceutical Co., Ltd., Shiga (JP)

( * ) Notice: Subject to any disclaimer, the term of this patent is extended or adjusted under 35 U.S.C. 154(b) by 0 days.

(21) Appl. No.: 15/355,315

(22) Filed: Nov. 18, 2016

(65) Prior Publication Data

US 2017/0304337 A1    Oct. 26, 2017

Related U.S. Application Data

(63) Continuation of application No. PCT/JP2016/072010, filed on Jul. 27, 2016, which is a continuation of application No. PCT/JP2016/065660, filed on May 27, 2016.

(30) Foreign Application Priority Data

Apr. 21, 2016 (JP) .................... 2016-085145

(51) Int. Cl.
A61K 31/706 (2006.01)
C07H 19/12 (2006.01)
A61K 47/48 (2006.01)

(52) U.S. Cl.
CPC ...... *A61K 47/48023* (2013.01); *A61K 31/706* (2013.01); *C07H 19/12* (2013.01)

(58) Field of Classification Search
None
See application file for complete search history.

(56) References Cited

U.S. PATENT DOCUMENTS 3,816,619 A     6/1974  Bergy et al.
2007/0072796 A1*  3/2007  Phiasivongsa ........ C12N 15/111
                                                514/430

FOREIGN PATENT DOCUMENTS

| DE | 1922702 A1 | 11/1969 |
| JP | 2009-509531 A | 3/2009 |
| WO | WO 2004/050665 A1 | 6/2004 |
| WO | WO 2004/050666 A1 | 6/2004 |
| WO | WO 2013/036846 A2 | 3/2013 |
| WO | WO 2016/057828 A1 | 4/2016 |

OTHER PUBLICATIONS

Bunseki, 2008, vol. 7, 332-336.

Chabner et al., "Purification and Properties of Cytidine Deaminase from Normal and Leukemic Granulocytes," The Journal of Clinical Investigation, Mar. 1974, 53:922-931.
Chu et al., "Particle Replication in Nonwetting Templates Nanoparticles with Tumor Selective Alkyl Silyl Ether Docetaxel Prodrug Reduces Toxicity," Nano Letters, 2014, 14(3):1472-1476.
Cihak, A., "Biological Effects of 5-Azacytidine in Eukaryotes," Oncology, 1974, 30(5):405-422.
Corey et al., "Protection of Hydroxyl Groups as tert-Butyldimethylsilyl Derivatives," Journal of the American Chemical Society, 1972, 94:6190-6191.
Corey et al., "Studies with trialkylsilyltriflates: New Syntheses and Applications," Tetrahedron Letters, 1981, 22(36):3455-3458.
Crouch et al., "Selective deprotection of silyl ethers," Tetrahedron, 2013, 69:2383-2417.
Crouch et al., "Selective monodeprotection of bis-silyl ethers," Tetrahedron, 2004, 60:5833-5871.
Greene et al., Protective Groups in Organic Synthesis, 1999, 26 pages.

(Continued)

*Primary Examiner* — Traviss C McIntosh, III
(74) *Attorney, Agent, or Firm* — Foley & Lardner LLP

(57) ABSTRACT

The present invention relates to a prodrug of 5-azacytidine or 2'-deoxy-5-azacytidine having remarkable stability against cytidine deaminase, a metabolic hydrolyzing enzyme in replacement of current injections (5-azacytidine or 2'-deoxy-5-azacytidine) which are clinically used as therapeutic agents for various myelomas including myelodysplastic syndrome. The present invention provides a compound represented by formula (1), or salt thereof,

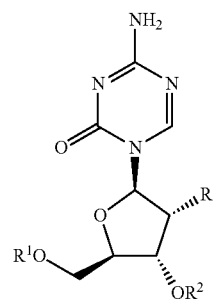

(1)

wherein, R is $OR^3$ or a hydrogen atom, $R^1$, $R^2$, and $R^3$ are each independently hydrogen atom or silyl group represented by formula (2):

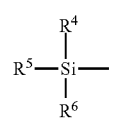

(2)

wherein, $R^4$, $R^5$, and $R^6$ are each independently alkyl group which may have a substituent, aryl group which may have a substituent, or arylalkyl group which may have a substituent, with the provision that $R^1$, $R^2$, and $R^3$ are not hydrogen atom simultaneously.

21 Claims, No Drawings

(56) References Cited

OTHER PUBLICATIONS

Krawczyk et al., "5-Azacytidine for the treatment of myelodysplastic syndromes," Expert Opinion on Pharmacotherapy, 2013, 14(9):1255-1268.
Navada et al., "Clinical development of demethylating agents in hematology," The Journal of Clinical Investigation, 2014, 124(1):40-46.
Nelson et al., "Selective Deprotection of Silyl Ethers," Synthesis, 1996, 1031-1069.
Parrott et al., "Incorporation and Controlled Release of Silyl Ether Prodrugs from PRINT Nanoparticles," Journal of the American Chemical Society, 2012, 134:7978-7982.
Piskala et al., "Preparation of some derivatives of 5-azacytidine and 2'-deoxy-5-azacytidine," Collect. Czech. Chem. Commun., 1996, 61:S23-S25.
Siedlecki et al., "Establishment and functional validation of a structural homology model for human DNA methyltransferase 1," Biochemical and Biophysical Research Communications, 2003, 306:558-563.

\* cited by examiner

SILYL ETHERIFIED DERIVATIVES OF 5-AZACYTIDINES IN CARBOHYDRATE MOIETY

TECHNICAL FIELD

The present invention relates to a compound which has remarkable stability against cytidine deaminase, a metabolic hydrolyzing enzyme, and can be used as a prodrug of 5-azacytidine or 2'-deoxy-5-azacytidine which is an antimyeloma agent.

TECHNICAL BACKGROUND

5-Azacytidine (also called as azacytidine or by the product name of Vidaza®) and 2'-deoxy-5-azacytidine (also called as decitabine or by the product name of Dacogen®) have following chemical structures, respectively. They are collectively referred to as "azacytidines or 5-azacytidines" in this specification. It has been known that these azacytidines inhibit protein synthesis and some enzymes by incorporating into RNA or DNA during nucleic acid bio-synthesis in frequently dividing cells, and show cytotoxicity (patent documents 1-2 and non patent document 1).

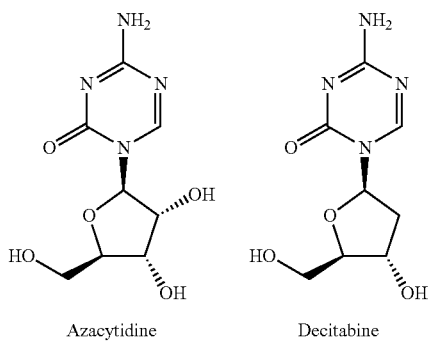 [SMILES: Nc1ncn([C@@H]2O[C@H](CO)[C@@H](O)[C@H]2O)c(=O)n1 ; Nc1ncn([C@H]2C[C@H](O)[C@@H](CO)O2)c(=O)n1]

Azacytidine      Decitabine

In the field of anti-oncogene promoter, when incorporating into DNA in cells, the azacytidines combine irreversibly with transferase of DNA methyl group relating to 5-methylation of the cytosine ring in highly risky myelodysplastic syndrome, in which the formation of a large amount of 5-methylated cytosine moiety has been confirmed, and cause enzyme inhibition. As a result, they promote the reactivation of anti-oncogenes and accordingly have been clinically used as therapeutic agents (5-azacytidine or 2'-deoxy-5-azacytidine) showing remarkable effects on highly risky myelodysplastic syndrome (non patent documents 2-3).

However, each of these azacytidines can be easily inactivated by cytidine deaminase, a metabolic hydrolyzing enzyme in blood and liver (less than 30 minutes of half-life, non patent document 4). As the current clinical situation, they can hardly be used effectively as therapeutic agents for patients with highly risky myelodysplastic syndrome. Accordingly, countermeasures are highly demanded.

On the other hand, silyl etherification of hydroxy groups can be expected to decrease boiling points of compounds and is applied in the field of analytical chemistry as a pretreatment method of samples for gas chromatography (particularly in case of trimethyl silyl etherification in hydroxy moiety, for example, non patent document 5 and the like). Besides, it can also be used in organic synthetic chemistry as a simple protective method for hydroxy group, since de-silylation is possible in mild conditions (non patent documents 6-11).

The following examples can be given as application of silyl etherification of hydroxy group. For the purpose of selective introduction of acyl group to 4-amino group of 5-azacytidine, firstly, all of the hydroxy groups in carbohydrate moiety are trimethyl silyl etherified by trimethyl silyl chloride in the presence of triethyl amine or pyridine and the like. Then, 4-amino group is acylated by carboxylic acid anhydride or acid chloride. After that, the protective group of trimethyl silyl in carbohydrate moiety is treated with methanol containing acetic acid or alcohol (non patent documents 12-13).

In addition, examples of investigation on silyl etherification of hydroxy group in search for prodrugs of pharmaceuticals can be given as follows. Pharmaceuticals can be released under acidic physiological conditions by crosslinkage at dialkyl silyl group between organic polymers having hydroxy groups on surface and pharmaceuticals, such as camptothecin, dasatinib, gemcitabine, and the like which have hydroxy groups in their molecules. It has been shown that they can possibly be used as DDS (drug delivery system) products (non patent document 14). Moreover, it is disclosed that docetaxel, an antitumor agent, can be used as a DDS product, in which docetaxel is released under acidic physiological conditions by becoming nanoparticles according to alkyl silyl etherification at 2'-hydroxy group of docetaxel (non patent document 15).

However, there are no investigational examples of silyl etherification in carbohydrate moiety in search for prodrugs of 5-azacytidine. Furthermore, there are no examples showing that cytidines become stable against cytidine deaminase, a metabolic hydrolyzing enzyme by silyl etherification of hydroxy group in carbohydrate moiety.

Regarding silyl etherification of hydroxy group in carbohydrate moiety of cytidines, various alkyl silyl etherifications of hydroxy group in carbohydrate moiety of Ara-C or gemcitabine have been reported. However, the stability and reactivity of these derivatives have not been disclosed and there are no examples of detailed disclosure about their use as chemotherapeutic agents (patent documents 3-4).

PRIOR ART DOCUMENTS

Patent Documents

1. Specification of U.S. Pat. No. 3,816,619
2. Specification of DE patent No. 1922702
3. Specification of WO 2004/050665
4. Specification of WO 2004/050666

Non Patent Documents

1. Oncology, 1974, vol. 30, No. 5, p. 405-422.
2. Expert Opinion on Pharmacotherapy, 2013, vol. 14, No. 9, p. 1255-1268.
3. The Journal of Clinical Investigation, 2014, vol. 124, No. 1, p. 40-46.
4. The Journal of Clinical Investigation, 1974, vol. 53, p. 922-931.
5. Bunseki, 2008, vol. 7, p. 332-336.
6. Journal of American Chemical Society, 1972, vol. 94, p. 6190-6191.
7. Tetrahedron Letters, 1981, vol. 22, p. 3455-3458.
8. Synthesis, 1996, p. 1031-1069.
9. Protective Groups in Organic Synthesis, 1999.

10. Tetrahedron, 2004, vol. 60, p. 5833-5871.
11. Tetrahedron, 2013, vol. 69, p. 2383-2417.
12. Collectin of Czechoslovak Chemical Communication, 1996, vol. 61, S23-S25
13. Biochemical and Biophysical Research Communication, 2003, vol. 306, p. 558-563.
14. Journal of American Chemical Society, 2012, vol. 134, p. 7978-7982.
15. Nano Letters, 2014, vol. 14, No. 3, p. 1472-1476.

SUMMARY OF THE INVENTION

Problems to be Solved by the Invention

An object of the present invention is to provide derivatives of 5-azacytidine or 2'-deoxy-5-azacytidine (referring to formula (1)), which have remarkable stability against cytidine deaminase, a metabolic hydrolyzing enzyme, and compounds which can release gradually the corresponding 5-azacytidines under physiological conditions and be used as prodrugs of 5-azacytidine or 2'-deoxy-5-azacytidine which are anti-myeloma agents.

Solutions to the Problem

In order to provide a more useful medicine for treating various myeloma including myelodysplastic syndrome, the present inventors have earnestly undertaken studies on finding novel compounds, which possess both excellent pharmacologic effects to incorporate into nucleic acid biosynthetic pathway in vivo and excellent physicochemical properties, and have remarkable stability against cytidine deaminase, a metabolic hydrolyzing enzyme. The present inventors have therefore synthesized various silyl etherified derivatives of 5-azacytidines in carbohydrate moiety and investigated their chemical reactivity. As the results, the present inventors found out that a silyl etherified derivative of 5-azacytidines in carbohydrate moiety with specific structure unexpectedly shows excellent properties as a medicine, which shows remarkable stability against cytidine deaminase, a metabolic hydrolyzing enzyme and excellent physicochemical properties, and finally completed the present invention.

That is, the above problems have been solved by the present invention described in [1] to [14] as below.

[1] A compound represented by formula (1), or salt thereof,

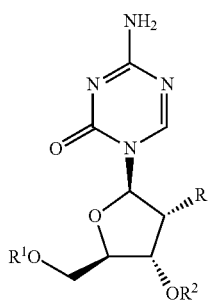

wherein R is $OR^3$ or hydrogen atom, $R^1$, $R^2$, and $R^3$ are each independently hydrogen atom or silyl group represented by formula (2):

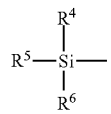

wherein, $R^4$, $R^5$, and $R^6$ are each independently alkyl group which may have a substituent, aryl group which may have a substituent, or arylalkyl group which may have a substituent, with the provision that $R^1$, $R^2$, and $R^3$ are not hydrogen atom simultaneously.

[2] The compound according to that described in [1], wherein $R^1$ is silyl group represented by the formula (2), $R^2$ and $R^3$ are hydrogen atom.

[3] The compound according to that described in [1], wherein $R^1$ and $R^2$ are each independently silyl group represented by the formula (2), $R^3$ is hydrogen atom.

[4] The compound according to that described in [1], wherein $R^1$, $R^2$, and $R^3$ are each independently silyl group represented by the formula (2).

[5] The compound according to that described in [1], wherein $R^1$ is hydrogen atom, $R^2$ and $R^3$ are each independently silyl group represented by the formula (2).

[6] The compound according to that described in [1], wherein $R^4$, $R^5$, and $R^6$ are each independently $C_1$ to $C_8$ alkyl group which may have a substituent, $C_6$ to $C_{10}$ aryl group which may have a substituent or $C_7$ to $C_{14}$ arylalkyl group which may have a substituent.

[7] The compound according to that described in [6], wherein $C_6$ to $C_{10}$ aryl group is phenyl group or naphthyl group.

[8] The compound according to that described in [6], wherein $C_7$ to $C_{14}$ arylalkyl group is benzyl group, phenethyl group, or naphthylmethyl group.

[9] A method for producing the compound, or salt thereof, according that described in [1], which includes reacting 5-azacytidine or 2'-deoxy-5-azacytidine with silyl halide.

[10] A pharmaceutical composition comprising each of the compounds, or salts thereof, according to those described in [1] to [8].

[11] The pharmaceutical composition according to that described in [10], which is a growth inhibitor of myeloma cells.

[12] The pharmaceutical composition according to that described in [10], which is an agent for preventing or treating various myeloma including myelodysplastic syndrome.

[13] A method of growth inhibition against myeloma cells in mammals, which includes an administration of each of the compounds, or salts thereof, according to those described in [1] to [8] to mammals in an effective amount.

[14] A method for preventing or treating myeloma including myelodysplastic syndrome in mammals, which includes an administration of each of the compounds, or salts thereof, according to those described in [1] to [8] to mammals in an effective amount.

Effects of the Invention

According to the present invention, by silyl etherification of hydroxy group of 5-azacytidine or 2'-deoxy-5-azacytidine in carbohydrate moiety, they become highly hydrophobic and therefore can be used in oral administrations. After being absorbed in intestines, they are inserted into frequently dividing tumor cells without being affected by cytidine deaminase, a metabolic hydrolyzing enzyme in blood or liver before gradually being hydrolyzed non-enzymatically under physiological conditions (for example, 37° C. and about pH5-7) and free the corresponding 5-azacytidines effectively at a suitable speed. As a result, they inhibit protein synthesis and some enzymes by incorporating into RNA and DNA via nucleic acid bio-synthetic pathway, and show cytotoxicity. On the other hand, they are expected to be used as therapeutic agents for various myelomas including myelodysplastic syndrome.

MODES TO CARRY OUT THE INVENTION

Terms used in the specification and claims have following meanings, unless otherwise stated.
The compound of the present invention, or salt thereof
The compound of the present invention is represented by formula (1) as below,

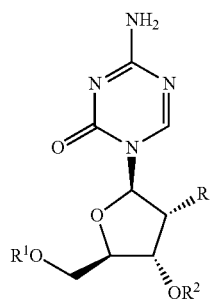

(1)

wherein R is $OR^3$ or a hydrogen atom, $R^1$, $R^2$, and $R^3$ are each independently hydrogen atom or silyl group represented by formula (2):

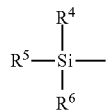

(2)

wherein, $R^4$, $R^5$ and $R^6$ are each independently alkyl group which may have a substituent, aryl group which may have a substituent, or arylalkyl group which may have a substituent, with the provision that $R^1$, $R^2$, and $R^3$ are not hydrogen atom simultaneously.

"Alkyl groups" refer to, unless otherwise limited, saturated aliphatic hydrocarbon groups, such as $C_1$ to $C_{20}$ straight or branched chains of alkyl groups. Examples include methyl, ethyl, propyl, iso-propyl, butyl, sec-butyl, iso-butyl, tert-butyl, pentyl, hexyl, heptyl, 1-methylhexyl, 5-methylhexyl, 1,1-dimethylpentyl, 2,2-dimethylpentyl, 4,4-dimethylpentyl, 1-ethylpentyl, 2-ethylpentyl, 1,1,3-trimethylbutyl, 1,2,2-trimethylbutyl, 1,3,3-trimethylbutyl, 2,2,3-trimethylbutyl, 2,3,3-trimethylbutyl, 1-propylbutyl, 1,1,2,2-tetramethylpropyl, octyl, 1-methylheptyl, 3-methylheptyl, 6-methylheptyl, 2-ethylhexyl, 5,5-dimethylhexyl, 2,4,4-trimethylpentyl, 1-ethyl-1-methylpentyl, nonyl, 1-methyloctyl, 2-methyloctyl, 3-methyloctyl, 7-methyloctyl, 1-ethylheptyl, 1,1-dimethylheptyl, 6,6-dimethylheptyl, decyl, 1-methylnonyl, 2-methylnonyl, 6-methylnonyl, 1-ethyloctyl, 1-propylheptyl, n-nonyl, n-decyl groups, and the like, preferably, $C_1$ to $C_6$ alkyl groups. Preferable examples of $C_1$ to $C_8$ alkyl groups are methyl, ethyl, propyl, iso-propyl, butyl, sec-butyl, iso-butyl, tert-butyl, pentyl, hexyl, heptyl, 1-methylhexyl, 5-methylhexyl, 1,1-dimethylpentyl, 2,2-dimethylpentyl, 4,4-dimethylpentyl, 1-ethylpentyl, 2-ethylpentyl, 1,1,3-trimethylbutyl, 1,2,2-trimethylbutyl, 1,3,3-trimethylbutyl, 2,2,3-trimethylbutyl, 2,3,3-trimethylbutyl, 1-propylbutyl, 1,1,2,2-tetramethylpropyl, octyl groups, and the like.

"Aryl groups" refer to monocyclic or bicyclic aromatic hydrocarbons, preferably $C_6$ to $C_{10}$ aryl groups, such as phenyl and naphthyl groups, and the like, more preferably phenyl group.

"Arylalkyl groups" refer to alkyl groups which are substituted by aryl groups, preferably phenyl $C_1$ to $C_6$ alkyl groups. The examples of phenyl $C_1$ to $C_6$ alkyl groups include, but are not limited to, benzyl, 1-phenylethyl, 2-phenylethyl, 3-phenylpropyl, 4-phenylbutyl, 5-phenylpentyl, 6-phenylhexyl groups, and the like.

"Alkyl group which may have a substituent, aryl group which may have a substituent or arylalkyl group which may have a substituent" means that silyl may have substituent or may not have substituent. In case of having substituent, its number may be 1 to 5, preferably 1 to 3 at any viable position of the alkyl, aryl, or arylalkyl groups. When the number of substituents is 2 or more, the substituents may be the same or different. Examples of the substituents include alkyl groups, halogen atoms, cyano group, nitro group, and the like. Preferable examples include alkyl groups or halogen.

"Halogen atoms" refer to fluorine, chlorine, bromine, or iodide atoms and the like. Preferable examples are fluorine and chlorine atoms.

Salts of the compound (1) of the present invention may be any salts as long as they are pharmaceutically acceptable. Their examples include, but are not limited to, acid added salts including inorganic salts (for example, hydrochloride, sulfate, hydrobromide, phosphate, and the like) and organic salts (for example, acetate, trifluoroacetate, succinate, maleate, fumarate, propionate, citrate, tartrate, lactate, oxalate, methane sulfonate, p-toluene sulfonate, and the like), etc.

The compound (1) of the present invention may be crystal. It can be in single crystalline form or a mixture of multiple crystalline forms. Crystals can be prepared by crystallization according to conventional methods.

In addition, the compound (1) of the present invention may be a solvate (for example, hydrate and the like). Both solvates and non-solvates (for example, non-hydrate and the like) are included in the compound (1).

Preparation Methods of the Compound (1) of the Present Invention

The compound (1) of the present invention can be prepared according to, for example following methods or other similar ones (For example, the silyl etherification methods disclosed in Corey, E. J. et al., J. Am. Chem. Soc., 94, 6190, 1972; Morita, T. et al., Tetrahedron Lett., 21, 835, 1980; Y. Kita, et al., Tetrahedron Lett., 4311, 1979 etc., and Lalonde, M., Chan, T. H., Synthesis, 817-845, 1985 etc. as reviews).

The compound (1), or salt thereof, can be prepared according to conventional methods or their similar ones. For example, commercially available 5-azacytidine or 2'-deoxy-5-azacytidine is reacted with a silylhalide compound in an appropriate solvent and presence of a base. As target compound, a silyl etherified derivative of 5-azacytidines in carbohydrate moiety can be obtained.

Silylhalide Compounds

The kind of silylhalide compounds is not particularly limited. Any silylhalide used in the art can be used for the methods of the present invention. For examples, trialkylsilylhalide, monoalkyldiarylsilylhalide, triarylsilylhalide compounds, and the like can be used. If a silylhalide compound has alkyl groups, for example, methyl, ethyl, n-propyl, iso-propyl, n-butyl, sec-butyl, iso-butyl, or tert-butyl groups and the like can be used as alkyl groups. Among them, methyl or ethyl group are preferable. If a silylhalide compound has aryl groups, phenyl group, and the like can be used. As halogen atoms which form the silylhalide compounds, chlorine, bromine, or iodine atoms, preferably chlorine atom can be used. More specific examples of silylhalide compounds include trimethylsilylchloride (which is also called as trimethylchlorosilane. The same applies to the following compounds.), triethylsilylchloride, tert-butyldimethylsilylchloride, tert-butyldiphenylsilylchloride, triphenylsilylchloride, and the like.

(Bases)

The bases used include organic and inorganic bases. Examples of organic bases include, but are not limited to, triethylamine, N,N-diisopropylethylamine, imidazole, pyridine, 4-dimethylaminopyridine (DMAP), n-butyl lithium, and potassium tert-butoxide, preferably, imidazole and pyridine. Examples of inorganic bases include, but are not limited to, sodium hydride, sodium carbonate, sodium hydrogen carbonate, potassium carbonate, potassium hydrogen carbonate, or cesium carbonate. Amounts of the bases used are preferably more than 1 mol or more of that of the starting material. Furthermore, normally the range of 1.0 to 10.0 mol based on 1 mol of the starting material; preferably the range of 2.0 to 6.0 mol and more preferably the range of 2.0 to 4.0 mol can be mentioned.

(Solvents)

From the viewpoints of smooth progress of reactions and the like, it is preferred that the reactions of the present invention are carried out in a solvent. Any solvent can be used for the reactions of the present invention as long as the reactions proceed.

Examples of the solvents for the reactions of the present invention include, but are not limited to, amines (such as N,N-dimethylformamide (DMF), N,N-dimethylacetamide (DMAC), N,N-diethylacetamide, N-methylpyrrolidone (NMP), and the like, preferably N,N-dimethylformamide (DMF), N,N-dimethylacetamide (DMAC), and N-methylpyrrolidone (NMP), more preferably N,N-dimethylformamide (DMF)) and sulfoxides (such as dimethyl sulfoxide (DMSO)), and the like. The solvents may be used in any amount as long as the reactions proceed. Amounts of the solvents for the reactions of the present invention can be adjusted appropriately by a person skilled in the art.

(Reaction Temperature)

Reaction temperature of the present invention is not particularly limited. From the viewpoints of improving yield, by-product control, economic efficiency, and the like, the range of −20 to 50° C. (minus 20 to plus 50° C.), preferable range of −10 to 30° C. (minus 10 to plus 30° C.) can be mentioned as examples in an embodiment.

(Reaction Time)

Reaction time of the present invention is not particularly limited. From the viewpoints of improving yield, by-product control, economic efficiency, and the like, the range of 0.5 to 120 hours, preferable range of 1 to 72 hours, more preferable range of 1 to 48 hours, even more preferable range of 1 to 24 hours can be mentioned as examples in an embodiment. However, reaction time of the present invention can be adjusted appropriately by a person skilled in the art.

Pharmaceutical Compositions of the Present Invention

The compound (1) of the present invention can be used as a safe medicine for mammals (such as humans, monkeys, cats, pigs, horses, cattle, mice, rats, guinea pigs, dogs, rabbits, and the like) as it is or as a pharmaceutical composition mixed with pharmaceutically acceptable carriers according to conventional methods.

Regarding the said pharmaceutically acceptable carriers, various conventional organic or inorganic substances can be used as formulation materials. Examples include solid formulations, such as excipients, lubricants, binding agents and disintegrating agents, liquid formulations, such as solvents, solubilizing agents, suspending agents, tonicity agents and buffers, and the like. Furthermore, formulation additives such as preservative agents, antioxidant agents, coloring agents, sweetening agents and the like can also be used when necessary.

Regarding dosage forms of the pharmaceutical compositions, oral preparations such as tablets, capsules (including soft capsules and microcapsules), granules, powders, syrups, emulsions, suspensions, sustained-release preparations, and the like, can be mentioned as examples. These can be administered orally and safely. However, they are not limited to these examples, because liquid formulations are also possible.

The pharmaceutical compositions can be prepared according to conventional methods in technical field of formulation. For example, methods described in The Japanese Pharmacopeia, et al. can be applied.

Use of the Compound (1) of the Present Invention

The compound (1) of the present invention can be used in many therapeutic and preventive ways. In a preferable embodiment, the compound (1) of the present invention is used for treatment of extraordinary various diseases which are sensitive to treatment with cytidine analogues or derivatives (such as decitabine or azacytidine). The preferable symptoms which can be treated with the compound (1) of the present invention include those accompanying with undesired or uncontrolled cell division, including hematological abnormality, benign tumors, various types of cancers (such as primary and metastatic tumors), restenosis (such as foci in coronary artery, carotid artery and cerebral artery), abnormal stimulation to endothelial cells (atherosclerosis), damage in body tissue caused by surgery, abnormal wound healing, abnormal angiogenesis, diseases causing tissue fibrosis, repetitive dyskinesia, high level angiodysplasia, and productive response followed by organ transplantation.

Regarding hematological abnormality, abnormal proliferation of hemocyte which may cause dysplasia of blood cells and hematological malignant diseases (such as various types of leukemia) are included. As the examples, acute myeloid leukemia, acute promyelocytic leukemia, acute lymphoblastic leukemia, chronic myeloid leukemia, myelodysplasia, and sickle cell anemia are included. However, they are not limited to these examples.

In several embodiments, hematological abnormality including genetic ones and/or hemoglobinopathy (such as sickle cell anemia) is treated with the compound (1) of the present invention. In some other embodiments, cancers including leukemia, preleukemia, and other myeloma related cancers, such as lung cancer accompanying with myelodysplastic syndrome (MDS), and non-small-cell lung cancer (NSCL) can also be treated with the compound (1) of the present invention. NSCL may include epidermoid cancer or squamous cell cancer, adenocarcinoma, and large carcinoma. MDS may include refractory anemia, refractory anemia having excessive transforming blast cells and myelomonocytic leukemia.

The pharmaceutical compositions used in the present invention comprise active ingredients in such effective amounts so that the purposes of treating and/or preventing the symptoms (for example, hematological abnormality (such as sickle cell anemia), MDS and/or cancer (for example, NSCL)) can be achieved.

The pharmaceutical compositions used in the present invention are provided as dosage forms for oral administration. The pharmaceutical compositions provided in this specification can be provided in solid, semi-solid, or liquid form for oral administrations, including buccal, lingual, and sublingual ones. Suitable dosage forms for oral administrations include, but are not limited to, tablets, capsules, pills, troches, medical candies, aromatized formulations, cachets, pellets, medicated chewing gum, granules, bulk powders, foaming formulations, non-foaming powders or granules, solutions, emulsions, suspension liquids, solutions, wafers, sprinkles, elixirs, and syrups. In addition to the active ingredient(s), the pharmaceutical compositions may contain binders, fillers, diluents, disintegrants, wetting agents, lubricants, glidants, coloring agents, dye-migration inhibitors, sweetening agents, and flavoring agents. Moreover, they can also contain one or more pharmaceutically acceptable carriers or excipients which are not limited to these examples.

Amounts of the compound (1) in the pharmaceutical compositions or dosage forms of the present invention can be, for example in any one of the ranges of about 1 to 2,000 mg, about 10 to 2,000 mg, about 20 to 2,000 mg, about 50 to 1,000 mg, about 100 to 500 mg, about 150 to 500 mg, or about 150 to 250 mg.

When using the compounds of the present invention as anticancer agents, their effective dosages can be properly chosen according to character and stage of cancer, therapeutic strategy, extent of metastasis, amount of tumor, body weight, age, sex, background of genetic race of patients, and the like. Pharmaceutically effective dosages are normally determined according to factors such as clinical observation of symptoms, stage of cancer and the like. Regarding the daily dosage, in case of administration to human, the ranges of about 0.01 to 10 mg/kg (about 0.5 to 500 mg for an adult having body weight of 60 kg), preferably about 0.05 to 5 mg/kg, more preferably about 0.1 to 2 mg/kg can be mentioned as examples. In addition, they may be administered at once or multiple times.

The stability of silyl etherified derivatives of 5-azacytidins in carbohydrate moiety obtained above was investigated in the presence of cytidine deaminase. As a result, among the derivatives of the present invention, each of those which have 5'-silyl ether group ($R^1$ is tri substituted silyl group in formula (1)) was fond to be remarkable stable in the presence of cytidine deaminase. It was confirmed that these 5-azacytidine-5'-silyl etherified derivatives hardly hydrolyze by cytidine deaminase, an enzyme existing in blood or liver. On the other hand, 5'-hydroxy forms of 5-azacytidine or 2'-deoxy-5-azacytidine (referring to formula (1)) decompose within 30 minutes under the above conditions.

In addition, the stability of silyl etherified derivatives of 5-azacytidines in carbohydrate moiety obtained above (referring to formula (1)) in similar environment with physiological conditions (for example, in PBS solution at 37° C.) was investigated. As the result, it has been confirmed that among the derivatives of the present invention, those having suitably selected substituents ($R^4$, $R^5$, and $R^6$) directly with silyl group are hydrolyzed at proper speed to provide the corresponding 5-azacytidines effectively. Additionally, it has also been confirmed that silyl etherified derivatives of 5-azacytidines in carbohydrate moiety which is hydrolyzed at proper speed show inhibitory activity against myeloma (for example, growth inhibition against lymphoblastoma cells).

Therefore, the silyl etherified derivatives of 5-azacytidines in carbohydrate moiety (referring to formula (1)) of the present invention which have remarkable stability against hydrolytic metabolic enzyme and proper hydrolysis reactivity under physiological conditions can possibly become prodrugs of therapeutic agents for various myeloma including myelodysplastic syndrome.

Regarding the silyl etherified derivatives of 5-azacytidines in carbohydrate moiety (referring to formula (1)), their preparation methods, experimental details about stability against cytidine deaminase, a metabolic hydrolyzing enzyme, hydrolysis reactivity in PBS solution, and anti myeloma activity are shown as below.

EXAMPLES

The examples provided below further illustrate the present invention. It is to be understood that the scope of the present invention is not limited in any way by the scope of the following examples.

In following examples, room temperature refers to about 15 to 30° C. The determinations of $^1$H-NMR and $^{13}$C-NMR were conducted with a JNM-ECZ 400R instrument (JEOL), in which CDCl$_3$, DMSO-d$_6$, or CD$_3$OD was used as a solvent, and chemical shifts (δ) from tetramethylsilane, an internal standard, are shown in ppm. Other terms used in the specification have the following meanings. s: singlet; d: doublet; t: triplet; m: multiplet; br: broad; br s: broad singlet; J: constant of J-coupling. In addition, mass determination of each compound was conducted with a Yamazen Smart Flash MS system.

Example 1

Synthesis of 5'-(trisubstituted) silyloxy-5-azacytidines (1a)

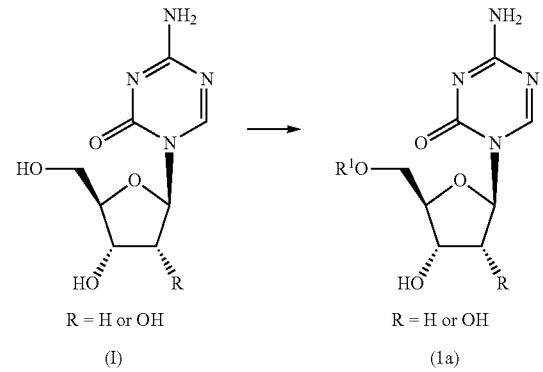

A suspension of a 5-azacytidines (I) (1 mM) in anhydrous N,N-dimethylformamide (3 mL) was added with imidazole (1.5 mM) and then added dropwise with a corresponding silyl chloride (1.2 mM) in about 10 minutes on an ice bath. The mixture was stirred for about 1 to 17 hours while being warmed gradually to room temperature until disappearance of starting material. The reaction solution was poured into 50 mL of a mixture of ethyl acetate/saturated saline (2:1) and extracted with ethyl acetate. The extract was washed twice with saturated saline (10 mL) and dried over anhydrous magnesium sulfate. After insoluble materials were removed by suction, the extract was concentrated to dryness under reduced pressure. The oily residue obtained was separated and purified with a silica gel column (Yamazen Smart Flash MS system) and as a white powder, a 5'-silyl etherified derivative of 5-azacytidines, (a compound, wherein in formula (1a), R is a hydroxy group or a hydrogen atom, $R^1$ is trisubstituted silyl group.), being a target compound, was obtained. This is referred to as synthetic method A hereafter.

Example 2

Synthesis of 3',5'-di (trisubstituted) silyloxy-5-azacytidines (1b)

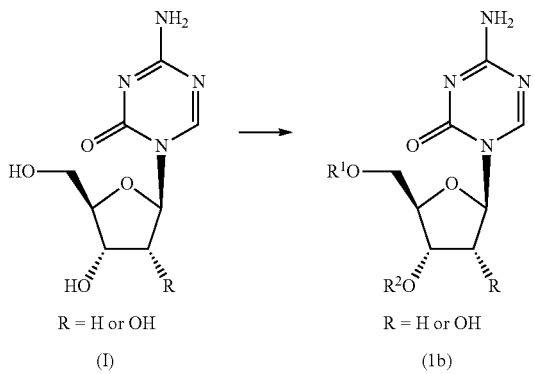

A suspension of a 5-azacytidines (I) (1 mM) in anhydrous N,N-dimethylformamide (3 mL) was added with imidazole (2 mM) and then added dropwise with a corresponding silyl chloride (1.5 mM) in about 10 minutes on an ice bath. The mixture was stirred for several hours while being warmed gradually to room temperature until disappearance of starting material. The reaction solution was poured into 50 mL of a mixture of ethyl acetate/saturated saline (2:1) and extracted with ethyl acetate. The extract was washed twice with saturated saline (10 mL) and dried over anhydrous magnesium sulfate. After insoluble materials were removed by suction, the extract was concentrated to dryness under reduced pressure. The oily residue obtained was separated and purified with a silica gel column (Yamazen Smart Flash MS system) and as a white powder, a 3',5'-di (silyl etherified derivative of 5-azacytidines (a compound, wherein in formula (1b), R is a hydroxy group or a hydrogen atom, $R^1$ and $R^2$ are trisubstituted silyl groups.), being a target compound, was obtained. This is referred to as synthetic method B hereafter.

Example 3

Synthesis of 2',3',5'-tri (trisubstituted) silyloxy-5-azacytidines (1c)

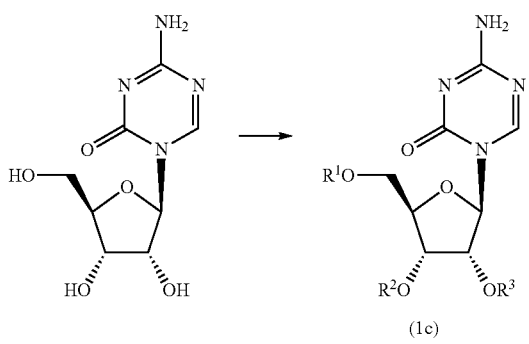

A suspension of 5-azacytidine (1 mM) in anhydrous N,N-dimethylformamide (2 mL) was added with imidazole (4 mM) and then added dropwise with a corresponding silyl chloride (3.5 mM) in about 10 minutes on an ice bath. The mixture was stirred for several hours while being warmed gradually to room temperature until disappearance of starting material. The reaction solution was poured into 50 mL of a mixture of ethyl acetate/saturated saline (2:1) and extracted with ethyl acetate. The extract was washed twice with saturated saline (10 mL) and dried over anhydrous magnesium sulfate. After insoluble materials were removed, the extract was concentrated to dryness under reduced pressure. The oily residue obtained was separated and purified with a silica gel column (Yamazen Smart Flash MS system) and as a white powder, a 2',3',5'-tri silyl etherified derivative of 5-azacytidines (a compound, wherein formula (1c), $R^1$, $R^2$ and $R^3$ are trisubstituted silyl groups.), being a target compound, was obtained. This is referred to as synthetic method C hereafter.

The reaction time, separation systems, separation yields and data obtained from instrumental analysis of silyl etherified derivatives of 5-azacytidines in carbohydrate moiety obtained in the investigation are shown as below.

(Compound A): 5'-O-Trimethylsilyl-5-azacytidine: (R=OH, $R^1$=trimethylsilyl Group in Formula (1a))

Synthetic method: Method A (Reaction time: about 1 hour, Solvent for column elution:ethyl acetate/methanol, Separation yield: 14%)

$^1$H-NMR (400 MHz, $CDCl_3$) δ: 8.53 (s, 1H), 6.20 (br, 1H), 5.81 (d, J=3.2 Hz, 1H), 5.69 (br, 1H), 5.30 (br, 1H), 4.38 (s, 1H), 4.25 (s, 2H), 3.87 (d, J=10.8 Hz, 1H), 3.72 (d, J=10.8 Hz, 1H), 3.45 (br, 1H), and 0.09 (s, 9H) ppm.

$^{13}$C-NMR ($CDCl_3$) δ: 166.7, 155.9, 155.5, 93.3, 87.8, 78.1, 72.6, 62.1, and −0.82 ppm.

Mass: 317.2 ($M^+$+1) (calcd. for $C_{11}H_{20}N_4O_5Si$, MW=316.39).

(Compound B): 5'-O-Trimethylsilyl-2'-deoxy-5-azacytidine: (R=H, $R^1$=trimethylsilyl Group in Formula (1a))

Synthetic method: Method A (Reaction time: about 1 hour, Solvent for column elution:ethyl acetate/methanol)

$^1$H-NMR (400 MHz, $CD_3OD$) δ: 8.66 (s, 1H), 6.13 (t, J=6.0 Hz, 1H), 4.35-4.42 (m, 1H), 3.67-4.02 (m, 9H), 2.34-2.50 (m, 1H), 2.20-2.32 (m, 1H), and 0.14 (s, 9H) ppm.

$^{13}$C-NMR ($CDCl_3$) δ: 166.3, 156.0, 154.1, 87.6, 86.8, 71.6, 62.3, 42.6, and 0.1 ppm.

Mass: 301.3 ($M^+$+1) (calcd. for $C_{11}H_{20}N_4O_4Si$, MW=300.13.)

(Compound C): 5'-O-Ethyldimethylsilyl-5-azacytidine: (R=OH, $R^1$=ethyldimethylsilyl Group in Formula (1a))

Synthetic method: Method A (Reaction time: about 1 hour, Solvent for column elution:ethyl acetate/methanol, Separation yield: 12%)

$^1$H-NMR (400 MHz, $CDCl_3$) δ: 8.56 (s, 1H), 6.61 (br, 1H), 5.94 (br, 1H), 5.83 (d, J=4.0 Hz, 1H), 4.31-4.34 (m, 1H), 4.23-4.28 (m, 2H), 3.91 (dd, J=11.6 and 2.4 Hz, 1H), 3.74 (dd, J=11.6 and 2.4 Hz, 1H), 0.92 (t, J=8.0 Hz, 3H), 0.56 (t, J=8.0 Hz, 2H), 0.09 (s, 3H), and 0.08 (s, 3H) ppm.

$^{13}$C-NMR ($CDCl_3$) δ: 166.5, 155.7, 155.6, 92.8, 87.3, 72.0, 62.0, 7.6, 6.6, and −3.03 ppm.

Mass: 331.2 (M$^+$+1) (calcd. for C$_{12}$H$_{22}$N$_4$O$_5$Si, MW=330.41).

(Compound D): 5'-O-(iso-Propyldimethylsilyl)-5-azacytidine: (R=OH, R$^1$=iso-propyldimethylsilyl Group in Formula (1a))

Synthetic method: Method A (Reaction time: about 1 hour, Solvent for column elution:ethyl acetate/methanol, Separation yield: 13%)
$^1$H-NMR (400 MHz, CDCl$_3$) δ: 8.56 (s, 1H), 6.81 (br, 1H), 6.08 (br, 1H), 5.85 (d, J=3.6 Hz, 1H), 5.62 (br, 1H), 4.31-4.33 (m, 1H), 4.24-4.28 (m, 2H), 3.92 (dd, J=11.6 and 2.4 Hz, 1H), 3.76 (dd, J=11.6 and 2.4 Hz, 1H), 3.72 (br, 1H), 0.93 (d, J=6.8 Hz, 6H), 0.79-0.88 (m, 1H), 0.07 (s, 3H), and 0.06 (s, 3H) ppm.
$^{13}$C-NMR (CDCl$_3$) δ: 166.4, 155.6, 155.4, 92.4, 87.0, 71.7, 62.2, 16.8, 16.7, 14.1, −4.7, and −4.8 ppm.
Mass: 345.2 (M$^+$+1) (calcd. for C$_{13}$H$_{24}$N$_4$O$_5$Si, MW=344.44).

(Compound E): 5'-O-(tert-Butyldimethylsilyl)-5-azacytidine: (R=OH, R$^1$=tert-butyldimethylsilyl Group in Formula (1a))

Synthetic method: Method A (Reaction time: about 3 hours, Solvent for column elution:ethyl acetate/methanol, Separation yield: 12%)
$^1$H-NMR (400 MHz, CDCl$_3$) δ: 8.50 (s, 1H), 6.32 (br, 1H), 5.81 (d, J=3.6 Hz, 1H), 5.76 (br, 1H), 5.45 (br, 1H), 4.35 (d, J=2.0 Hz, 1H), 4.24-4.29 (m, 2H), 3.93 (dd, J=12.0 and 2.4 Hz, 1H), 3.78 (dd, J=12.0 and 2.0 Hz, 1H), 3.54 (br, 1H), 0.86 (s, 9H), and 0.06 (s, 6H) ppm.
$^{13}$C-NMR (CDCl$_3$) δ: 167.2, 156.4, 156.0, 93.6, 88.2, 78.1, 72.8, 63.7, 26.5, 18.9, −5.0, and −5.1 ppm.
Mass: 359.2 (M$^+$+1) (calcd. for C$_{14}$H$_{26}$N$_4$O$_5$Si, MW=358.47).

(Compound F): 5'-O-Benzyldimethylsilyl-5-azacytidine: (R=OH, R$^1$=benzyldimethylsilyl Group in Formula (1a))

Synthetic method: Method A (Reaction time: about 17 hours, Solvent for column elution:ethyl acetate/methanol, Separation yield: 23%)
$^1$H-NMR (400 MHz, CDCl$_3$) δ: 8.45 (s, 1H), 7.19-7.25 (m, 2H). 7.06-7.10 (m, 1H). 6.98-7.00 (m, 2H). 6.18 (br, 1H), 5.77 (d, J=4.0 Hz, 1H), 5.67 (br, 1H), 5.27 (br, 1H), 4.31-4.32 (m, 1H), 4.10-4.16 (m, 2H), 3.84 (dd, J=8.0 and 2.4 Hz, 1H), 3.68 (dd, J=11.6 and 1.6 Hz, 1H), 3.38 (br, 1H), 2.16 (s, 2H), 0.12 (s, 3H), and 0.11 (s, 3H) ppm.
$^{13}$C-NMR (CDCl$_3$) δ: 166.6, 155.9, 155.4, 138.1, 128.5, 128.3, 124.7, 93.1, 87.5, 72.3, 62.5, 26.3, −2.53, and −2.58 ppm.
Mass: 393.2 (M$^+$+1) (calcd. for C$_{17}$H$_{24}$N$_4$O$_5$Si, MW=392.48).

(Compound G): 5'-O-(n-Octyldimethylsilyl)-5-azacytidine: (R=OH, R$^1$=n-Octyldimethylsilyl Group in Formula (1a))

Synthetic method: Method A (Reaction time: about 1 hour, Solvent for column elution:ethyl acetate/methanol, Separation yield: 18%)
$^1$H-NMR (400 MHz, CD$_3$OD) δ: 8.78 (s, 1H), 5.79 (d, J=1.6 Hz, 1H), 4.13-4.19 (m, 2H), 4.07 (dt, J=6.8 and 2.0 Hz, 1H), 4.03 (dd, J=12.0 and 2.4 Hz, 1H), 3.82 (dd, J=12.0 and 2.0 Hz, 1H), 1.22-1.42 (m, 8H), 0.86-0.93 (m, 4H), 0.62-0.72 (m, 3H), 0.15 (s, 6H), and 0.14-0.18 (m, 2H) ppm.
$^{13}$C-NMR (CD$_3$OD) δ: 156.6, 156.0, 155.2, 90.8, 84.1, 75.2, 68.5, 60.5, 33.2, 31.8, 29.1, 29.0, 22.9, 22.4, 15.5, 13.1, −3.6, and −3.7 ppm.
Mass: 415.4 (M$^+$+1) (calcd. for C$_{18}$H$_{34}$N$_4$O$_5$Si, MW=414.23).

(Compound H): 5'-O-(n-Octyldimethylsilyl)-2'-deoxy-5-azacytidine: (R=H, R$^1$=n-octyldimethylsilyl Group in Formula (1a))

Synthetic method: Method A (Reaction time: about 1 hour, Solvent for column elution:ethyl acetate/methanol, Separation yield: 24%)
$^1$H-NMR (400 MHz, CD$_3$OD) δ: 8.65 (s, 1H), 6.12 (t, J=5.6 Hz, 1H), 4.34-4.37 (m, 1H), 4.00-4.02 (m, 1H), 3.91-3.95 (m, 1H), 3.76-3.79 (m, 1H), 2.45 (ddd, J=13.6, 6.4, and 4.4 Hz, 1H), 2.24 (m, 1H), 1.27-1.34 (m, 8H), 0.87-0.89 (m, 4H), 0.61-0.63 (m, 3H), and 0.12 (s, 6H).
$^{13}$C-NMR (CD$_3$OD) δ: 156.2, 155.8, 155.1, 87.9, 86.7, 70.5, 61.8, 41.6, 33.2, 31.8, 29.1, 22.4, 15.6, 13.1, −1.38, −2.96, −3.73, and −3.83 ppm.
Mass: 399.3 (M$^+$+1) (calcd. for C$_{18}$H$_{34}$N$_4$O$_4$Si, MW=398.23).

(Compound I): 5'-O-(tert-Butyldiphenylsilyl)-5-azacytidine: (R=OH, R$^1$=tert-butyldiphenylsilyl Group in Formula (1a))

Synthetic method: Method A (Reaction time: about 2 hours, Solvent for column elution:ethyl acetate/methanol, Separation yield: 48%)
$^1$H-NMR (400 MHz, CD$_3$OD) δ: 8.63 (s, 1H), 7.69-7.72 (m, 4H), 7.38-7.47 (m, 6H), 5.81 (d, J=2.4 Hz, 1H), 4.32 (dd, J=7.2 and 5.2 Hz, 1H), 4.23 (dd, J=5.2 and 2.4 Hz, 1H), 4.03-4.09 (m, 2H), 3.82 (dd, J=11.6 and 2.8 Hz, 1H), and 1.08 (s, 9H) ppm.
$^{13}$C-NMR (CD$_3$OD) δ: 166.4, 155.5, 155.0, 135.4, 135.2, 132.5, 132.3, 129.6, 127.5, 90.8, 83.9, 74.7, 68.7, 62.5, and 26.0 ppm.
Mass: 483.4 (M$^+$+1) (calcd. for C$_{24}$H$_{30}$N$_4$O$_5$Si, MW=482.60).

(Compound J): 5'-O-Triethylsilyl-5-azacytidine: (R=OH, R$^1$=triethylsilyl Group in Formula (1a))

Synthetic method: Method A (Reaction time: about 1 hour, Solvent for column elution:ethyl acetate/methanol, Separation yield: 10%)
$^1$H-NMR (400 MHz, CD$_3$OD) δ: 8.77 (s, 1H), 5.80 (d, J=2.0 Hz, 1H), 4.22 (dd, J=6.8 and 4.8 Hz, 1H), 4.15 (dd, J=4.8 and 2.0 Hz, 1H), 4.03-4.10 (m, 2H), 3.85 (dd, J=11.6 and 2.0 Hz, 1H), 1.00 (t, J=8.4 Hz, 9H), and 0.67-0.74 (m, 6H) ppm.
$^{13}$C-NMR (CD$_3$OD) δ: 163.0, 152.3, 151.5, 87.1, 80.4, 71.6, 64.7, 57.1, 2.07, and 0.00 ppm.
Mass: 359.2 (M$^+$+1) (calcd. for C$_{14}$H$_{26}$N$_4$O$_5$Si, MW=358.47).

(Compound K): 5'-O-Triethylsilyl-2'-deoxy-5-azacytidine: (R=H, R$^1$=triethylsilyl Group in Formula (1a))

Synthetic method: Method A (Reaction time: about 1 hour, Solvent for column elution:ethyl acetate/methanol, Separation yield: 81%)

¹H-NMR (400 MHz, CDCl₃) δ: 8.62 (s, 1H), 6.26 (t, J=6.0 Hz, 1H), 6.25 (br, 1H), 5.58 (br, 1H), 4.47-4.51 (m, 1H), 4.09-4.11 (m, 1H), 3.93 (dd, J=10.8 and 2.4 Hz, 1H), 3.82 (dd, J=11.6 and 2.0 Hz, 1H), 2.64-2.70 (m, 1H), 2.66 (br, 1H), 2.23 (dt, J=12.0 and 6.4 Hz, 1H), 0.96 (t, J=8.0 Hz, 9H), and 0.63 (t, J=8.0 Hz, 6H) ppm.

¹³C-NMR (CDCl₃) δ: 166.3, 156.0, 154.1, 87.6, 86.8, 71.6, 62.3, 42.6, 6.7, and 4.1 ppm.

Mass: 343.3 (M⁺+1) (calcd. for $C_{14}H_{26}N_4O_4Si$, MW=342.47).

(Compound L): 5'-O-(iso-Propyldiethylsilyl)-5-azacytidine: (R=OH, R¹=iso-propyldiethylsilyl Group in Formula (1a))

Synthetic method: Method A (Reaction time: about 1 hour, Solvent for column elution:ethyl acetate/methanol, Separation yield: 21%)

¹H-NMR (400 MHz, CDCl₃) δ: 8.56 (s, 1H), 7.04 (br, 1H), 6.21 (br, 1H), 5.85 (d, J=2.8 Hz, 1H), 5.70 (br, 1H), 4.28 (s, 3H), 3.98 (d, J=11.2 Hz, 1H), 3.81 (d, J=11.2 Hz, 1H), 3.79 (br, 1H), 0.93-0.99 (m, 13H), and 0.61-0.65 (m, 4H) ppm.

¹³C-NMR (CDCl₃) δ: 166.4, 155.6, 155.5, 92.2, 87.0, 71.5, 62.5, 17.3, 17.2, 12.5, 7.0, 3.0, and 2.9 ppm.

Mass: 373.3 (M⁺+1) (calcd. for $C_{15}H_{28}N_4O_5Si$, MW=372.49).

(Compound M): 3',5'-Di(O-trimethylsilyl)-2'-deoxy-5-azacytidine: (R=H, R¹=R²=trimethylsilyl Group in Formula (1b))

Synthetic method: Method B (Reaction time: about 1 hour, Solvent for column elution:ethyl acetate/methanol, Separation yield: 70%)

¹H-NMR (400 MHz, CDCl₃) δ: 8.69 (s, 1H), 6.17 (dd, J=6.4 and 4.4 Hz, 1H), 5.89 (br s, 1H), 5.44 (br s, 1H), 4.36 (q, J=5.6 Hz, 1H), 3.94-3.96 (m, 1H), 3.88 (dd, J=11.6 and 2.8 Hz, 1H), 3.71 (dd, J=12.0 and 2.4 Hz), 2.50 (q, J=6.8 Hz, 1H), 2.17-2.23 (m, 1H), 0.16 (s, 9H), and 0.12 (s, 9H) ppm.

¹³C-NMR (CDCl₃) δ: 166.4, 156.2, 154.0, 87.6, 86.6, 69.7, 60.8, 42.2, 0.10, and −0.69 ppm.

Mass: 373.3 (M⁺+1) (calcd. for $C_{14}H_{28}N_4O_4Si_2$, MW=372.16.)

(Compound N): 3',5'-Di(O-n-octyldimethylsilyl)-2'-deoxy-5-azacytidine: (R=H, R¹=R²=n-octyldimethylsilyl Group in Formula (1b))

Synthetic method: Method B (Reaction time: about 2 hours, Solvent for column elution:ethyl acetate/n-hexane, Separation yield: 54%)

¹H-NMR (400 MHz, CD₃OD) δ: 8.61 (s, 1H), 6.10 (t, J=5.2 Hz, 1H), 4.46 (dd, J=10.0 and 4.8 Hz, 1H), 3.97 (dd, J=6.4 and 2.8 Hz, 1H), 3.88 (dd, J=11.6 and 3.2 Hz, 1H), 3.76 (dd, J=11.2 and 2.4 Hz, 1H), 2.41 (dt, J=13.6 and 6.0 Hz, 1H), 2.24 (dt, J=13.6 and 5.6 Hz, 1H), 1.29-1.34 (m, 24H), 0.87-0.91 (m, 6H), 0.61-0.68 (m, 4H), 0.14 (s, 6H), and 0.12 (s, 6H) ppm.

¹³C-NMR δ: 166.7, 155.8, 155.0, 88.0, 86.5, 70.8, 61.2, 41.6, 33.3, 31.8, 29.16, 29.12, 29.11, 23.0, 22.9, 22.4, 16.0, 15.6, 13.2, −2.78, −2.89, −3.57, and −3.75 ppm.

Mass: 569.5 (M⁺+1) (calcd. for $C_{28}H_{56}N_4O_4Si_2$, MW=568.38).

(Compound P): 3',5'-Di(O-triethylsilyl)-5-azacytidine: (R=OH, R¹=R²=triethylsilyl Group in Formula (1b))

Synthetic method: Method B (Reaction time: about 1 hour, Solvent for column elution:ethyl acetate/n-hexane, Separation yield: 25%)

¹H-NMR (400 MHz, CDCl₃) δ: 8.58 (s, 1H), 6.43 (br, 1H), 5.92 (d, J=3.2 Hz, 1H), 5.58 (br, 1H), 4.34 (t, J=5.2 Hz, 1H), 4.12 (br, 1H), 4.08 (dt, J=6.0 and 2.0 Hz, 1H), 3.98 (dd, J=11.6 and 2.4 Hz, 1H), 3.75 (dd, J=11.2 and 2.4 Hz, 1H), 3.09 (br, 1H), 0.97 (dt, J=8.0 and 5.2 Hz, 18H), and 0.61-0.70 (m, 12H) ppm.

¹³C-NMR (CDCl₃) δ: 166.2, 156.1, 154.0, 90.3, 84.9, 76.0, 70.2, 61.1, 6.73, 6.64, 4.62, and 4.10 ppm.

Mass: 473.4 (M⁺+1) (calcd. for $C_{20}H_{40}N_4O_5Si_2$, MW=472.73).

(Compound Q): 3',5'-Di(O-triethylsilyl)-2'-deoxy-5-azacytidine: (R=H, R¹=R²=triethylsilyl Group in Formula (1b))

Synthetic method: Method B (Reaction time: about 2 hours, Solvent for column elution:ethyl acetate/n-hexane, Separation yield: 54%)

¹H-NMR (400 MHz, CDCl₃) δ: 8.67 (s, 1H), 6.19 (dd, J=6.4 and 4.8 Hz, 1H), 5.61 (br, 1H), 5.38 (br, 1H), 4.41 (q, J=4.8 Hz, 1H), 3.96-3.98 (m, 1H), 3.91 (dd, J=11.6 and 2.8 Hz, 1H), 3.76 (dd, J=11.6 and 2.0 Hz, 1H), 2.51 (dt, J=13.2 and 6.0 Hz, 1H), 2.15-2.21 (m, 1H), 0.92-0.99 (m, 18H), and 0.56-0.68 (m, 12H) ppm.

¹³C-NMR (CDCl₃) δ: 166.4, 156.2, 154.0, 88.0, 86.6, 70.2, 61.5, 42.7, 6.8, 4.7, and 4.2 ppm.

Mass: 457.4 (M⁺+1) (calcd. for $C_{20}H_{40}N_4O_4Si_2$, MW=456.73).

(Compound R): 2',3',5'-Tri(O-trimethylsilyl)-5-azacytidine: (R¹=R²=R³=trimethylsilyl Group in Formula (1c))

Synthetic method: Method C (Reaction time: about 1 hour, Solvent for column elution:ethyl acetate/n-hexane, Separation yield: 64%)

¹H-NMR (400 MHz, CDCl₃) δ: 8.82 (s, 1H), 6.23 (br, 1H), 5.70 (s, 1H), 5.49 (br, 1H), 4.09-4.16 (m, 3H), 4.01 (dd, J=12.0 and 1.2 Hz, 1H), 3.70 (dd, J=11.6 and 1.2 Hz, 1H), 0.20 (s, 9H), 0.19 (s, 9H), and 0.13 (s, 9H) ppm.

¹³C-NMR (CDCl₃) δ: 166.5, 156.4, 153.9, 91.2, 82.7, 76.4, 68.3, 59.3, 0.4, 0.2, and −0.7 ppm.

Mass: 461.3 (M⁺+1) (calcd. for $C_{17}H_{36}N_4O_5Si_3$, MW 460.75).

(Compound S): 2',3',5'-Tri(O-ethyldimethylsilyl)-5-azacytidine: (R¹=R²=R³=dimethylethylsilyl Group in Formula (1c))

Synthetic method: Method C (Reaction time: about 1 hour, Solvent for column elution:ethyl acetate/n-hexane, Separation yield: 67%)

¹H-NMR (400 MHz, CDCl₃) δ: 8.80 (s, 1H), 6.27 (br, 1H), 5.71 (d, J=0.8 Hz, 1H), 5.49 (br, 1H), 4.08-4.16 (m, 3H), 4.01 (dd, J=12.0 and 0.8 Hz, 1H), 3.72 (dd, J=11.6 and 0.8 Hz, 1H), 0.90-1.01 (m, 9H), 0.57-0.74 (m, 6H), 0.19 (s, 3H), 0.16 (s, 9H), 0.10 (s, 3H), and 0.09 (s, 3H) ppm.

$^{13}$C-NMR (CDCl$_3$) δ: 166.5, 156.3, 153.9, 91.1, 82.8, 68.4, 59.6, 8.6, 8.3, 7.7, 6.8, −1.8, −1.9, −2.1, −2.8, and −3.0 ppm.

Mass: 503.4 (M$^+$+1) (calcd. for C$_{20}$H$_{42}$N$_4$O$_5$Si$_3$, MW=502.83).

(Compound T): 2',3',5'-Tri(O-iso-propyldimethylsilyl)-5-azacytidine: (R$^1$=R$^2$=R$^3$=iso-propyldimethylsilyl Group in Formula (1c))

Synthetic method: Method C (Reaction time: about 1 hour, Solvent for column elution:ethyl acetate/n-hexane, Separation yield: 74%)

$^1$H-NMR (400 MHz, CDCl$_3$) δ: 8.76 (s, 1H), 6.68 (br, 1H), 5.71 (d, J=1.2 Hz, 1H), 5.55 (br, 1H), 4.09-4.17 (m, 3H), 4.03 (d, J=12.0 Hz, 1H), 3.74 (d, J=11.6 Hz, 1H), 0.92-1.02 (m, 21H), 0.18 (s, 3H), 0.14 (s, 3H), 0.12 (s, 3H), 0.11 (s, 3H), and 0.07 (s, 6H) ppm.

$^{13}$C-NMR (CDCl$_3$) δ: 166.5, 156.2, 153.9, 90.9, 83.0, 76.4, 68.7, 59.9, 17.0, 16.9, 14.9, 14.6, 14.3, −3.4, −3.5, −3.9, −4.1, −4.5, and −4.8 ppm.

Mass: 545.4 (M$^+$+1) (calcd. for C$_{23}$H$_{48}$N$_4$O$_5$Si$_3$, MW=544.91).

(Compound U): 2',3',5'-Tri(O-tert-butyldimethylsilyl)-5-azacytidine: (R$^1$=R$^2$=R$^3$=tert-butyldimethylsilyl Group in Formula (1c))

Synthetic method: Method C (Reaction time: about 15 hours, Solvent for column elution:ethyl acetate/n-hexane, Separation yield: 67%)

$^1$H-NMR (400 MHz, CDCl$_3$) δ: 8.73 (s, 1H), 6.46 (br, 1H), 5.73 (d, J=2 Hz, 1H), 5.45 (br, 1H), 4.17 (dd, J=3.6 and 1.6 Hz, 1H), 4.06-4.13 (m, 3H), 3.80 (d, J=1.2 Hz, 0.5H), 3.77 (d, J=1.6 Hz, 0.5H), 0.96 (s, 9H), 0.91 (s, 9H), 0.89 (s, 9H), 0.21 (s, 3H), 0.15 (s, 3H), 0.13 (s, 3H), 0.11 (s, 3H), and 0.06 (s, 3H) ppm.

$^{13}$C-NMR (CDCl$_3$) δ: 171.9, 161.7, 159.4, 95.9, 88.7, 81.5, 74.6, 66.3, 31.7, 31.4, 24.2, 23.6, 23.5, 1.45, 1.31, 0.52, 0.44, and 0.22 ppm.

Mass: 587.5 (M$^+$+1) (calcd. for C$_{26}$H$_{54}$N$_4$O$_5$Si$_3$, MW=586.99).

(Compound V): 2',3',5'-Tri(O-triethylsilyl)-5-azacytidine: (R$^1$=R$^2$=R$^3$=triethylsilyl Group in Formula (1c))

Synthetic method: Method C (Reaction time: about 1 hour, Solvent for column elution:ethyl acetate/n-hexane, Separation yield: 99%)

$^1$H-NMR (400 MHz, CDCl$_3$) δ: 8.78 (s, 1H), 5.87 (br, 1H), 5.73 (d, J=1.2 Hz, 1H), 4.10-4.17 (m, 3H), 4.04 (dd, J=11.6 and 1.6 Hz, 1H), 3.77 (dd, J=11.6 and 1.2 Hz, 1H), 0.92-1.01 (m, 27H), and 0.57-0.78 (m, 18H) ppm.

$^{13}$C-NMR (CDCl$_3$) δ: 166.4, 156.3, 153.8, 90.6, 83.0, 76.4, 68.8, 60.2, 6.82, 6.80, 6.74, 4.80, 4.75, and 4.07 ppm.

Mass: 587.5 (M$^+$+1) (calcd. for C$_{26}$H$_{54}$N$_4$O$_5$Si$_3$, MW=586.99).

(Compound W): 2',3',5'-Tri-(O-iso-propyldiethylsilyl)-5-azacytidine: (R$^1$=R$^2$=R$^3$=iso-propyldiethylsilyl Group in Formula (1c))

Synthetic method: Method C (Reaction time: about 1 hour, Solvent for column elution:ethyl acetate/n-hexane, Separation yield: 74%)

$^1$H-NMR (400 MHz, CDCl$_3$) δ: 8.76 (s, 1H), 6.38 (br, 1H), 5.75 (d, J=2.0 Hz, 1H), 5.47 (br, 1H), 4.07-4.22 (m, 4H), 3.81 (d, J=10.4 Hz, 1H), 0.94-1.05 (m, 36H), and 0.63-0.76 (m, 15H) ppm.

$^{13}$C-NMR (CDCl$_3$) δ: 166.4, 156.4, 153.9, 90.3, 83.2, 69.3, 60.6, 17.4, 17.3, 13.1, 13.0, 12.4, 7.2, 7.1, 7.0, 3.9, 3.8, 3.7, 3.0, and 2.8 ppm.

Mass: 629.5 (M$^+$+1) (calcd. for C$_{29}$H$_{60}$N$_4$O$_5$Si$_3$, MW=629.07).

Example 4

Compound X: 2',3'-Di(O-tert-butyldimethylsilyl)-5-azacytidine: (R$^1$=H, R$^2$=R$^3$=tert-butyldimethylsilyl Group in Formula (1c))

200 mg of compound U (0.34 mM) was dissolved in 5 mL of anhydrous tetrahydrofuran. 0.34 mL of tetrabutyl ammonium chloride (1 M of tetrahydrofuran solution, 0.34 mM) was added on an ice bath and stirred for 2.5 hours. The reaction solution was diluted with 30 mL of a mixture of ethyl acetate/saturated saline (2:1) and extracted with ethyl acetate. The extract was washed twice with saturated saline (10 mL) and dried over anhydrous magnesium sulfate. After insoluble materials were removed, the extract was concentrated under reduced pressure. The residue obtained was separated and purified with a silica gel column (eluted with chloroform:methanol=10:1) and as a white powder, compound X was obtained as a target compound (Separation yield: 37%).

$^1$H-NMR (400 MHz, CDCl$_3$) δ: 8.22 (s, 1H), 5.45 (br, 1H), 5.30 (d, J=5.6 Hz, 1H), 4.82 (dd, J=6.0 and 4.8 Hz, 1H), 4.23 (dd, J=4.4 and 3.2 Hz, 1H), 4.11-4.13 (m, 1H), 3.92-3.95 (m, 1H), 3.78-3.80 (m, 1H), 3.66-3.71 (m, 1H), 0.91 (s, 9H), 0.87 (s, 9H), 0.09 (s, 3H), 0.08 (s, 3H), 0.07 (s, 3H), and 0.02 (s, 3H) ppm.

$^{13}$C-NMR (CDCl$_3$) δ: 170.9, 163.3, 158.6, 100.1, 92.1, 77.4, 76.8, 66.7, 30.7, 23.0, 22.8, 4.90, 0.43, 0.24, 0.10, and 0.00 ppm.

Test Example 1

Stability of Silyl Etherified Derivatives of 5-azacytidines in Carbohydrate Moiety Against Cytidine Deaminase About 1 mg each of the silyl etherified derivatives of 5-azacytidines in carbohydrate moiety (referring to formula (1a)) was dissolved in 1 mL of acetonitrile. 10 μL of the solution was diluted with 1 mL of PBS. 10 μL of PBS solution of cytidine deaminase was added to the solution and stirred at 37° C. for about 1 hour. 1 mL of acetonitrile was added to the reaction solution and separated by centrifugation. The supernatant was analyzed with HPLC. As examples, the analytical results in cases of 5'-O-(tert-butyldimethylsilyl)-5-azacytidine (compound E), 5'-O-(triethylsilyl)-5-azacytidine (compound J), and 5'-O-triethylsilyl-2'-deoxy-5-azacytidine (compound K) are shown in Table 1.

Cytidine deaminase: CDA (1-146aa), Human, His-tagged, Recombinant cytidine deaminase (ATGen)

HPLC conditions:
Column: CAPCELL PAK ADME (4.6 mm×150 mm, particle size: 3 μm)
Elution:eluate A=Purified water containing 10 mM ammonium formate
eluate B=Acetonitrile
Gradient mode: A:B=99:1→5:95/30 minutes Flow rate: 1.0 mL/min
Oven temperature: 40° C.
Detection: UV240 nm

TABLE 1

| Starting material | Change in HPLC pattern |
|---|---|
| 5-Azacytidine | The peak of the starting material disappeared completely after 30 minutes. |
| 2'-Deoxy-5-azacytidine | The peak of the starting material disappeared completely after 30 minutes. |
| 5'-O-(t-butyldimethylsilyl)-5-azacytidine (compound E) | Almost no change in the peak of the starting material was confirmed even after 1 hour. |
| 5'-O-(triethylsilyl)-5-azacytidine (compound J) | Almost no change in the peak of the starting material was confirmed even after 1 hour. |
| 5'-O-triethylsilyl-2'-deoxy-5-azacytidine (compound K) | Almost no change in the peak of the starting material was confirmed even after 1 hour. |

Accordingly, the silyl etherified derivatives of 5-azacytidines in carbohydrate moiety of the present invention are extremely stable against cytidine deaminase. On the other hand, 5-azacytidine and 2'-deoxy-5-azacytidine disappeared completely under the above reaction conditions.

Test Example 2

Non-Enzymatic Hydrolysis of Silyl Etherified Derivatives of 5-azacytidines in Carbohydrate Moiety About 1 mg each of the silyl etherified derivatives of 5-azacytidines in carbohydrate moiety (referring to formula (1a)), such as 5'-O-triethylsilyl-5-azacytidine (compound J) was dissolved in 1 mL of acetonitrile. 5 μL of the solution was added to 100 μL of 10 mM PBS solution and stirred at 37° C. The reactions were traced by HPLC analysis. As the results, the production of 5-azacytidine was confirmed. Meanwhile, the formation of productions of other catabolites was not confirmed. In addition, the same result was obtained in case of 5'-O-triethylsilyl-2'-deoxy-5-azacytidine (compound K) and the production of corresponding deskill form (2'-deoxy-5-azacytidine) was confirmed.

HPLC conditions were same as those in test example 1.

TABLE 2

| | 5-Azacytidine or 2'-deoxy-5-azacytidine (%) | | |
|---|---|---|---|
| | After 4 hours | After 8 hours | After 24 hours |
| 5'-O-triethylsilyl-5-azacytidine (compound J) | 16 | 22 | 62 |
| 5'-O-triethylsilyl-2'-deoxy-5-azacytidine (compound K) | 10 | 12 | 48 |

Test Example 3

Anti-Myeloma Activity of Silyl Etherified Derivatives of 5-azacytidines in Carbohydrate Moiety To the solutions containing RPMI-8226 myeloma cells (about 4000), solutions of silyl etherified derivatives of 5-azacytidines in carbohydrate moiety at concentrations of 0.0033 μM, 0.01 μM, 0.033 μM, 0.1 μM, 0.33 μM, 1 μM, 3.3 μM, 10 μM, 33 μM, or 100 μM were added. After incubation in RPMI-1640 (containing 10% FBS and 1% Penn-strep) for 72 hours, cell count was determined and $IC_{50}$ values were calculated as inhibitory effect against cell proliferation (referring to Journal of Clinical Pathology, 2006, 59, 947-951.).

TABLE 3

| Compound | $IC_{50}$ (μM) |
|---|---|
| 5'-O-triethylsilyl-5-azacytidine (compound J) | 0.656 |
| 5'-O-triethylsilyl-2'-deoxy-5-azacytidine (compound K) | 0.27 |
| 2'-Deoxy-5-azacytidine | 0.03 |

INDUSTRIAL APPLICABILITY

According to the present invention, a prodrug compound having remarkable stability against cytidine deaminase, a metabolic hydrolyzing enzyme, can be provided to clinical practice potentially in replacement of current injections (5-azacytidine and 2'-deoxy-5-azacytidine) which are clinically used as therapeutic agents for various myeloma including myelodysplastic syndrome.

What is claimed is:

1. A compound represented by formula (1), or salt thereof,

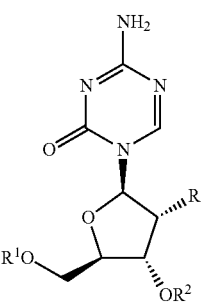

(1)

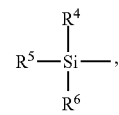

(2)

wherein R is $OR^3$ or hydrogen atom, wherein either a) $R^1$ is a silyl group represented by formula (2):

while $R^2$ and $R^3$ are each hydrogen atom; or b) $R^1$ is hydrogen atom, while $R^2$ and $R^3$ are each independently a silyl group represented by the formula (2)

wherein $R^4$, $R^5$, and $R^6$ are each independently alkyl group which may have a substituent, aryl group which may have a substituent, or arylalkyl group which may have a substituent.

2. The compound according to claim 1, wherein $R^1$ is silyl group represented by the formula (2), while $R^2$ and $R^3$ are each hydrogen atom.

3. The compound according to claim 1, wherein $R^1$ is hydrogen atom, while $R^2$ and $R^3$ are each independently a silyl group represented by the formula (2).

4. The compound according to claim 1, wherein $R^4$, $R^5$, and $R^6$ are each independently $C_1$ to $C_8$ alkyl group which may have a substituent, $C_6$ to $C_{10}$ aryl group which may have a substituent or $C_7$ to $C_{14}$ arylalkyl group which may have a substitute.

5. The compound according to claim 4, wherein the $C_6$ to $C_{10}$ aryl group is phenyl group or naphthyl group.

6. The compound according to claim 4, wherein the $C_7$ to $C_{14}$ arylalkyl group is benzyl group, phenethyl group or naphthylmethyl group.

7. The compound according to claim 2, wherein $R^4$, $R^5$, and $R^6$ are each independently $C_1$ to $C_8$ alkyl group which may have a substituent, $C_6$ to $C_{10}$ aryl group which may have a substituent or $C_7$ to $C_{14}$ arylalkyl group which may have a substitute.

8. The compound according to claim 2, wherein $R^4$, $R^5$, and $R^6$ are each independently $C_1$ to $C_8$ alkyl group which may have a substituent.

9. A method for producing the compound or salt thereof, according to claim 1, which includes reacting 5-azacytidine or 2'-deoxy-5-azacytidine with silyl halide.

10. A pharmaceutical composition, which comprises the compound, or salt thereof, according to claim 1.

11. A method for treatment of a symptom, which is selected from the group consisting of hematological abnormality, benign tumors, primary and metastatic tumors, restenosis, abnormal stimulation to endothelial cells, damage in body tissue caused by surgery, abnormal wound healing, abnormal angiogenesis, repetitive dyskinesia, high level angiodysplasia, and productive response followed by organ transplantation, the method comprising administering to a patient in need thereof the compound or salt thereof of claim 1.

12. A method for producing a compound or a salt thereof, which comprises reacting 5-azacytidine or 2'-deoxy-5-azacytidine with silyl halide, wherein the compound is a compound of formula (1):

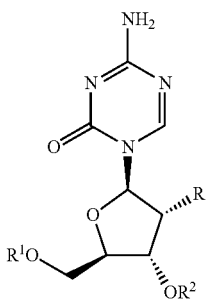

(1)

wherein R is $OR^3$ or hydrogen atom, $R^1$, $R^2$, and $R^3$ are each independently a hydrogen atom or silyl group represented by formula (2):

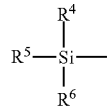

(2)

wherein, $R^4$, $R^5$, and $R^6$ are each independently an alkyl group which may have a substituent, aryl group which may have a substituent, or arylalkyl group which may have a substituent, with the provision that $R^1$, $R^2$, and $R^3$ are not hydrogen atom simultaneously and 2',3',5'-tri(O-trimethylsilyl)-5-azacytidine is excluded.

13. The method of claim 12, wherein $R^1$ is a silyl group represented by the formula (2), and $R^2$ and $R^3$ are hydrogen.

14. The method of claim 12, wherein $R^1$ and $R^2$ are each independently a silyl group represented by the formula (2), and $R^3$ is hydrogen.

15. The method of claim 12, wherein $R^1$, $R^2$, and $R^3$ are each independently a silyl group represented by the formula (2).

16. The method of claim 12, wherein $R^1$ is hydrogen, and $R^2$ and $R^3$ are each independently a silyl group represented by the formula (2).

17. The method of claim 12, wherein $R^4$, $R^5$, and $R^6$ are each independently a $C_1$ to $C_8$ alkyl group which may have a substituent, $C_6$ to $C_{10}$ aryl group which may have a substituent or $C_7$ to $C_{14}$ arylalkyl group which may have a substitute.

18. The method of claim 17, wherein the $C_6$ to $C_{10}$ aryl group is a phenyl group or naphthyl group.

19. The method of claim 17, wherein the $C_7$ to $C_{14}$ arylalkyl group is a benzyl group, phenethyl group or naphthylmethyl group.

20. The method of claim 13, wherein $R^4$, $R^5$, and $R^6$ are each independently a $C_1$ to $C_8$ alkyl group which may have a substituent, $C_6$ to $C_{10}$ aryl group which may have a substituent or $C_7$ to $C_{14}$ arylalkyl group which may have a substituent.

21. The method of claim 13, wherein $R^4$, $R^5$, and $R^6$ are each independently a $C_1$ to $C_8$ alkyl group which may have a substituent.

\* \* \* \* \*